US010969342B1

(12) United States Patent
Gao et al.

(10) Patent No.: US 10,969,342 B1
(45) Date of Patent: Apr. 6, 2021

(54) PESTICIDE DROPLET LEAF TRANSMEMBRANE ABSORPTION OBSERVATION APPARATUS

(71) Applicant: JIANGSU UNIVERSITY, Jiangsu (CN)

(72) Inventors: Jianmin Gao, Jiangsu (CN); Xu Liu, Jiangsu (CN)

(73) Assignee: JIANGSU UNIVERSITY, Jiangsu (CN)

(*) Notice: Subject to any disclaimer, the term of this patent is extended or adjusted under 35 U.S.C. 154(b) by 82 days.

(21) Appl. No.: 16/498,854

(22) PCT Filed: May 17, 2017

(86) PCT No.: PCT/CN2017/084643
§ 371 (c)(1),
(2) Date: Sep. 27, 2019

(87) PCT Pub. No.: WO2018/176602
PCT Pub. Date: Oct. 4, 2018

(30) Foreign Application Priority Data

Mar. 31, 2017 (CN) ........................ 201710206078.2

(51) Int. Cl.
*G01N 1/00* (2006.01)
*G01N 21/84* (2006.01)
(Continued)

(52) U.S. Cl.
CPC ............. *G01N 21/84* (2013.01); *G01N 21/01* (2013.01); *G01N 33/0098* (2013.01); *G01N 2021/8466* (2013.01); *G01N 2201/0238* (2013.01)

(58) Field of Classification Search
CPC ................. G01N 1/2813; G01N 1/286; G01N 2001/284; G01N 21/32; G01N 1/2806; G02B 21/32
(Continued)

(56) References Cited

U.S. PATENT DOCUMENTS

2005/0069207 A1* 3/2005 Zakrzewski ........... G06K 9/629
382/190
2009/0040367 A1* 2/2009 Zakrzewski ........... G06K 9/629
348/370

FOREIGN PATENT DOCUMENTS

CN 103207196 A 7/2013
CN 204630944 U 9/2015
(Continued)

OTHER PUBLICATIONS

Gao, Jianmin, et al., "Variation characters of droplet coverage area in leaf droplet water uptake process." Journal of Drainage and Irrigation Machinery Engineering, Mar. 2012, 30(2): 198-202.

*Primary Examiner* — Md M Rahman
(74) *Attorney, Agent, or Firm* — Saliwanchik, Lloyd & Eisenschenk

(57) ABSTRACT

A pesticide droplet leaf transmembrane absorption observation apparatus: an outer anti-mist glass cover (13) is shrouded over a lower base plate (14) to form an outer anti-mist chamber, used for accommodating a whole plant, a support frame (12) being arranged inside an outer atomising chamber, an inner anti-mist glass cover (9) being shrouded over an upper top plate of the support frame (12) to form an observation chamber, an outer atomising nozzle (6) and an inner atomising nozzle (8) respectively being inserted into the outer anti-mist chamber and the observation chamber, a temperature controller (2) respectively being connected to the outer atomising nozzle (6) and the inner atomising nozzle (8); a temperature sensor (7) is arranged
(Continued)

inside the observation chamber and is connected to a data collection computer (1), a leaf pressing mechanism (10) being arranged inside the observation chamber and being used for pressing the leaves of the plant; a first digital camera (3) and a first microscope (4) and a second digital camera (15) and a second microscope (16) are respectively arranged above and to the side of the anti-mist glass cover (13). By means of constructing a 100% humidity small environment comprising only the leaves and the droplets thereupon, the measurement error caused by the entire plant absorbing droplets can be reduced to the greatest extent.

7 Claims, 2 Drawing Sheets

(51) Int. Cl.
*G01N 33/00* (2006.01)
*G01N 21/01* (2006.01)

(58) Field of Classification Search
USPC .......................................................... 356/36
See application file for complete search history.

(56) References Cited

FOREIGN PATENT DOCUMENTS

| | | | |
|---|---|---|---|
| CN | 105277495 | A | 1/2016 |
| CN | 105300993 | A | 2/2016 |
| JP | 2003080236 | A | 3/2003 |

* cited by examiner

PESTICIDE DROPLET LEAF TRANSMEMBRANE ABSORPTION OBSERVATION APPARATUS

CROSS REFERENCE TO RELATED APPLICATIONS

This application is a National Stage Application of International Application Number PCT/CN2017/084643, filed May 17, 2017; which claims priority to Chinese Application No. 201710206078.2, filed Mar. 31, 2017.

BACKGROUND OF THE INVENTION

Technical Field

The invention relates to a cross-membrane absorption on leaf observation device for a pesticide spray, which belongs to the field of agricultural engineering.

Related Art

The leaf surface spraying technology of pesticides is widely used in pest control, pathogen inhibition, and weed removal. However, the utilization efficiency of the existing pesticide spraying technology is relatively low. This low efficiency causes a huge waste of pesticides, increases the extra cost of crop production, and aggravates the environmental pollution. Therefore, the improvement of the leaf to the pesticide mist is improved. The absorption effect is one of the important ways to solve the above problems. Research on the transmembrane absorption of pesticide mist droplets depends on the observation device. The existing observing devices focus on the absorption process of the leaf surface, but they neglect to observe and study the mist surface absorption process on the leaf surface.

The existing fog droplet absorption observation device has the following deficiencies:

1. In an environment with 100% humidity, the plant will absorb a large amount of moisture from the extremely moist ambient air in addition to the droplets, which will affect the test accuracy.

2. The test system only takes pictures of the absorption process of the droplets from the top-view direction, and the side-view images absorbed by the droplets cannot be obtained, resulting in the inability to obtain the spatial form of the droplets absorption process.

SUMMARY OF THE INVENTION

In order to overcome the deficiencies of the prior art, the present invention provides a cross-membrane absorption on leaf observation device for a pesticide spray. By fixing the position of the leaf, an environment with 100% humidity including only the leaf and the mist located on the leaf is established, and the real morphological change information of the pesticide mist droplets absorbed on the leaf surface is obtained through the stereoscopic microscopic test system, and the maximum reduction is minimized. The measurement error caused by the whole plant's absorption of droplets.

The specific technical solution adopted by the present invention is as follows:

a cross-membrane absorption on leaf observation device for a pesticide spray is characterized in that it includes a data acquisition computer (1), a temperature and humidity controller (2), a first digital camera (3), a first microscope (4), an illumination lamp (5), an external Interior atomization nozzle (6), a temperature and humidity sensor (7), and an interior atomization nozzle (8), internal anti-fog glass cover (9), leaf pressing mechanism (10), support frame (12), external anti-fog glass cover (13), bottom plate (14), second digital camera (15), and second microscope (16).

The external anti-fog glass cover (13) is shrouded on the bottom plate (14) to form an external anti-fog room for placing the whole plant and the support frame (12) is placed in the external atomization chamber. The internal anti-fog glass cover (9) is shrouded on the top plate of the support frame (12), and it constitutes an observation room with the top plate. The external atomizing nozzle (6) and the internal atomizing nozzle are respectively inserted into the external anti-fog room and the observation room. The temperature and humidity controller (2) is connected with the external atomizing nozzle (6) and the internal atomizing nozzle respectively through two data lines. Control the external atomizing nozzle (6) and the an Interior atomization nozzle (8) to control the humidity in the atomizing chamber.

The temperature and humidity sensor (7) is placed in the observation room and is connected with the data acquisition computer (1) through a data line for detecting the temperature and humidity in the interior anti-fog glass room. the leaf pressing mechanism is arranged in the observation room above the upper top plate of the support frame (12) for compacting plant leaves.

The illumination lamp (5) is located above the external anti-fog glass cover (13). The first digital camera (3) and the first microscope (4) are placed above the external anti-fog glass cover (13) to obtain the absorption process of the mist droplets on the front surface of the leaf, the relative position between the first microscope (4) and the external anti-fog glass cover can be adjusted; the second digital camera (15) and the second microscope (16) are placed lateral to the external anti-fog glass cover and can adjust the relative position between the microscope and the external anti-fog glass cover for obtaining the leaf The absorption process of the side fog droplets; the first digital camera (3) and the second digital camera (15) are respectively connected to the data acquisition computer (1) through two data acquisition lines; the data acquisition computer (1) is used to receive, observe and process the first digital camera (3) and the second digital camera (15) transmits the image of the mist droplet absorption process over the leaf surface and monitors the humidity inside the internal anti-fog glass cover (9).

Further, the blade pressing mechanism is a manual mechanical leaf edge compactor, By the first circular arc edge block (17), Second circular arc edge block (18), A circular arc-shaped edge block with a single protruding rod without a through hole (19), Single sticking rod and double through hole fixing block (20), A single sticking rod and a single through hole fixing block (21) and six connecting rods (22-27) are composed. The central axis of the cylindrical through hole of the fixing block with the through hole is parallel to the central axis of the protruding rod with the protruding rod and the protruding rod of the fixing block, and the nominal diameter of the through hole and the protruding rod Both are 10 mm, and the connection of any through hole and the extension rod adopts a clearance fit. The protruding rod of the circular arc-shaped edge block of the single protruding rod without the through hole (19) is first inserted into the same side of the fixing block of the single protruding rod and the single through hole (21), Then, the two through holes of the single sticking rod and double through hole fixing block (20) are respectively placed on the arc-shaped leaf edge pressing block having a single protruding rod without a through hole (19) and a protruding rod of a fixing piece of a single protruding rod and a single through hole (21). Finally, all the briquettes and the fixed blocks are connected by the six connecting rods to form 10 living hinges. The fixing block of the single extension rod and the single through hole (21) is fixedly connected to the support frame by welding, the heights of the first circular arc edge block (17) and the second circular leaf edge block (18) are both 15 mm, the protruding rod length of the circular arc-shaped edge block of the single protruding rod without the through hole (19) is 60 mm, and the length of the protruding rod of the single protruding rod and the single through hole fixing block (21) is 45 mm, the length of the protruding rod of the single protruding rod and the fixing block of the double through hole 20 is 30 mm, the thickness of the six connecting rods (22-27) is 3 mm Further, the temperature and humidity controller (2) has two knobs respectively for controlling the atomization amount, and the inner atomizing nozzle and the external atomizing nozzle (6) are stepped horns with exponential transition sections and low frequency ultrasonic fog. The shower head has a main body vibration frequency of 45-60 kHz.

Further, the first digital camera (3) and the second digital camera (15) respectively photograph the enlarged images of the first microscope (4) and the second microscope (16).

Further, the temperature and humidity sensor (7) model is DHT11, the temperature measurement range is 0° C.-50° C., the humidity measurement range is 20%-95%, and the humidity measurement error is ±5%.

Further, the external anti-fog glass cover has five surfaces, the size of which is 620 mm in length, 380 mm in width, 304 mm in height, and is made of ordinary glass coated with conductive material ITO and silicon oxide, and the external anti-fog glass cover. The upper surface has a nozzle fixing hole with a diameter of 13 mm.

Further, the internal anti-fog glass cover (9) has five faces, the size of which is 180 mm in length, 180 mm in width, and 50 mm in height, and is made of ordinary glass coated with conductive material ITO and silicon oxide, and the internal anti-fog glass cover (9). The upper surface has a fixing hole with a diameter of 13 mm.

The advantages of the present invention are:

1. The existing fog droplet absorption observation system is to place the entire plant in a 100% humidity environment. In addition to absorbing the droplets, the plants will also absorb moisture from the extremely moist ambient air in large quantities, which will affect the test accuracy. In contrast, the present invention establishes a 100% humidity environment including only the leaves and the mists located thereon, and minimizes the measurement error caused by the absorption of droplets by the entire plant.

2. Observing the leaf from both the positive and lateral directions so that a more complete morphological change of the droplet absorption process can be obtained.

3. A reliable fixation of the observed leaf is achieved and the observed area is increased as much as possible depending on the actual surface area of the observed leaf by designing a manual mechanical leaf pressing mechanism (10).

In the FIG. 10—Data acquisition computer, 2—Temperature and humidity controller, 3—First digital camera, 4—First microscope, 5—Illumination lamp, 6—External Atomizing Nozzle, 7—Temperature and humidity sensor, 8—Interior atomization nozzle, 9—Internal anti-fog cover, 10—Leaf compression mechanism, 11—Plant leaf, 12—Support frame, 13—External anti-fog cover, 14—Bottom plate, 15—Second digital camera, 16—Second microscope.

DESCRIPTION OF EXEMPLARY EMBODIMENTS

The present invention will be further described below with reference to the accompanying drawings and specific embodiments. However, the scope of protection of the present invention is not limited to these.

Figure 1:
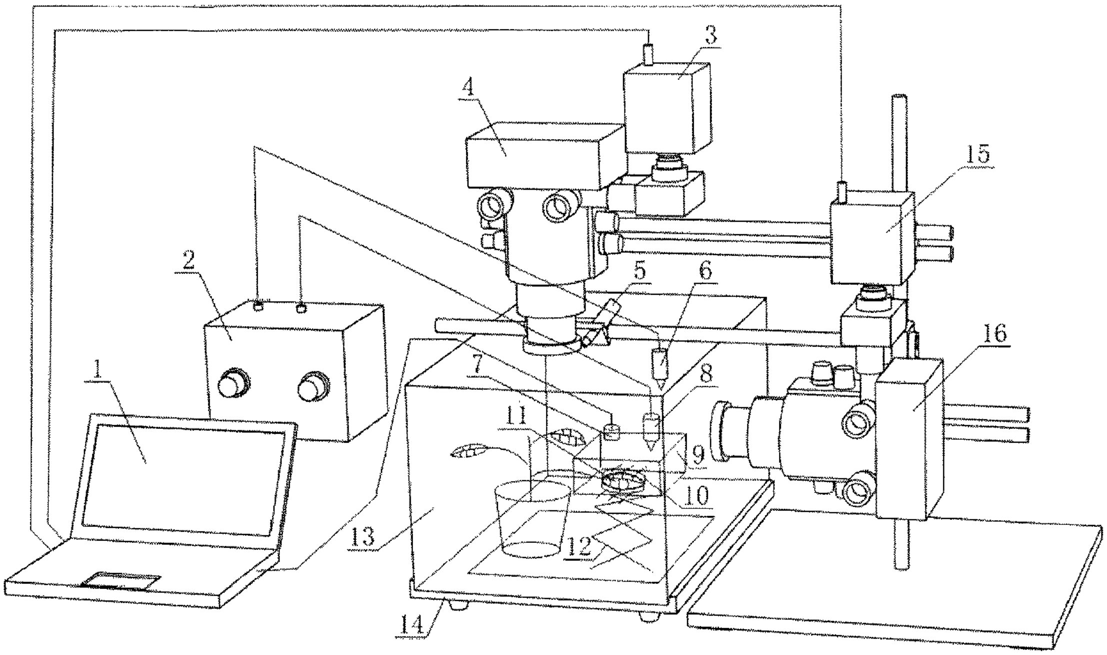
FIG. 1 is a schematic diagram of the structure of the cross-membrane absorption on leaf observation device for a pesticide spray according to the present invention.

As shown in FIG. 1, this drawing is a schematic diagram of the basic structure of the cross-membrane absorption on leaf observation device for a pesticide spray according to the present invention. The data acquisition computer 1, the temperature and humidity controller 2, the first digital camera 3, and the first microscope 4, Light 5, external atomizing nozzle 6, temperature and humidity sensor 7, internal atomizing nozzle 8, internal anti-fog glass cover 9, leaf pressing mechanism 10, plant leaf 11, support frame 12, external anti-fog glass cover 13 The bottom plate 14, the second digital camera 15, the second microscope 16, and the like are shown in FIG.

Figure 2:
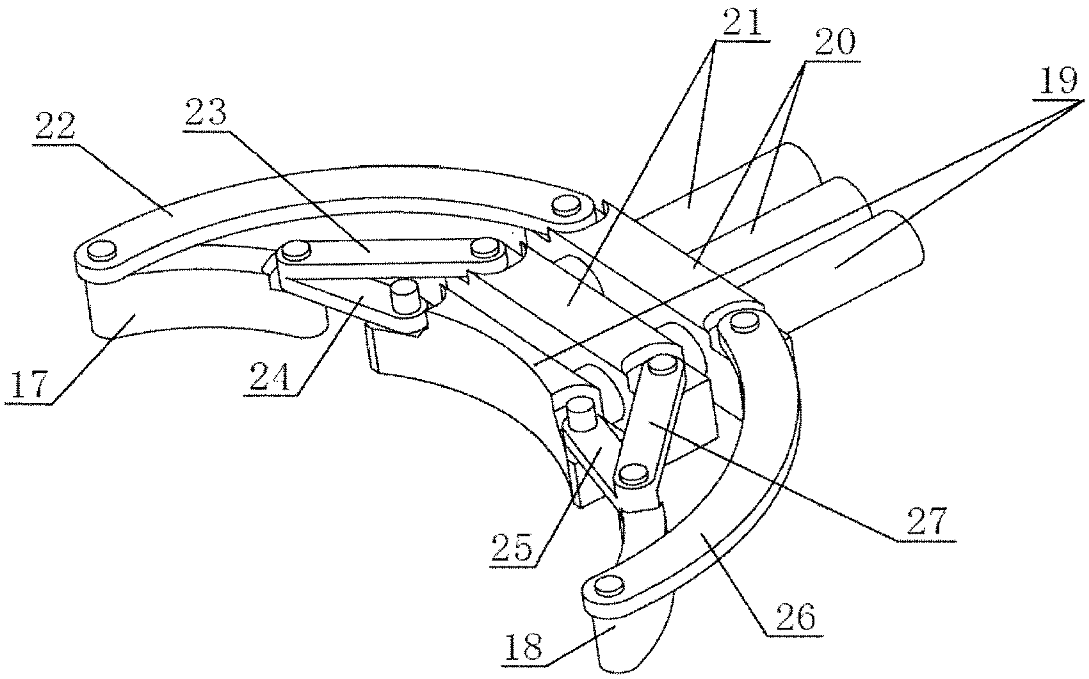
FIG. 2 is a schematic structural view of the manual mechanical leaf pressing mechanism (10)

The structure of the leaf pressing mechanism 10 in the present invention is shown in FIG. 2, and it is a manual mechanical leaf edge presser. The first arc-shaped leaf edge presser 17 and the second arc-shaped leaf edge presser 18 are used alone. The arc-shaped leaf edge press Interior atomization nozzle with no through-hole protruding from the rod 19, the fixing Interior atomization nozzle with single extension rod and double-passage hole 20, the fixing Interior atomization nozzle with single extension rod and single-passage hole 21 and the six connecting rods 22-27 are formed The central axis of the cylindrical through-hole of the fixed Interior atomization nozzle with the through-hole is parallel to the central axis of the projecting block with the protruding block and the protruding piece of the fixed Interior atomization nozzle in the same horizontal plane, and the nominal value of the all through-hole and the protruding block diameters are 10 mm, any connection between the through-hole and the protruding rod adopts clearance fit, The extension block of the circular curved leaf with a single protruding rod with no pass hole is inserted into the same side hole of the single extension block and the fixed Interior atomization nozzle of the single-pass hole 21, and then the two through-holes of the single projecting rod and the fixed Interior atomization nozzle of the double through-hole 20 are respectively placed on the arc-shaped leaf edge compact and the single projecting rod and the single-passage of the single projecting rod without the through-hole 19. Finally, using the six connecting rods 22-27 to connect all the pressure pieces and the fixing pieces to form 10 living hinges. The single projecting rod and the single through-hole fixing Interior atomization nozzle 21 are fixedly connected to the support frame 12 by welding, Manually advancing and pulling out the single-projecting rod without through-hole arc-shaped leaf edge press Interior atomization nozzle 19 and the single projecting rod and the protruding rod of the double through-hole fixing Interior atomization nozzle 20 to adjust the both and the single protruding rod. The relative position between the fixed Interior atomization nozzle 21 and the single through-hole is adjusted according to the size of the leaf so as to obtain as large a surface area as possible. The height of the first arc-shaped leaf edge pressure piece 17 and the second arc-shaped leaf edge pressure piece 18 is 15 mm, and the protrusion of the arc-shaped leaf edge pressure piece 19 without the through-hole of the single projecting rod is extended. The length of the rod is 60 mm, the length of the projecting rod of the single projecting rod and the single through-hole fixing Interior atomization nozzle 21 is 45 mm, and the length of the projecting rod of the single projecting rod and the fixed Interior atomization nozzle 20 of the double through-hole is 30 mm. Each of the six connecting rods 22-27 has a thickness of 3 mm.

Figure 3:
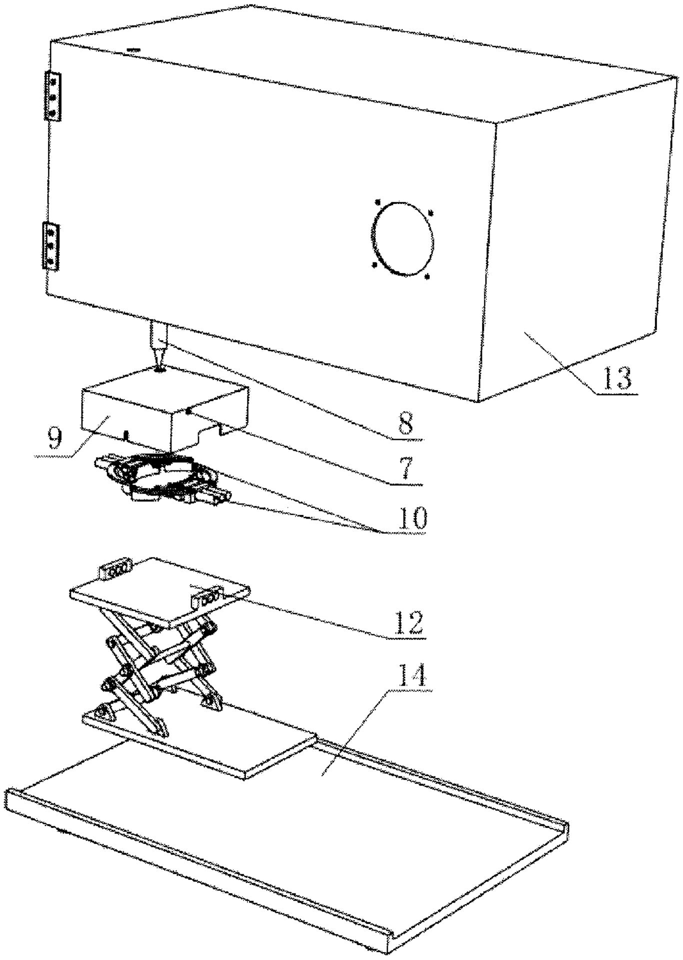
FIG. 3 is a schematic exploded view of inner and external atomization chambers in the present invention.

FIG. 3 is a schematic exploded view of the inner and external spray chambers in the present invention. The external anti-fog glass cover 13 and the bottom plate 14 constitute an external anti-fog glass room for placing the entire plant. In the external anti-fog glass room, the internal anti-fog glass cover 9 and the upper top plate of the support frame 12 constitute an inner anti-fog glass room, which is an observation room. The leaf to be observed is placed on the surface of the top plate on the support frame 12 in the interior anti-fog glass chamber, and then the leaf pressing mechanism 10 presses on the leaf, The extending rods are respectively inserted into the positioning holes on the top plate of the support frame 12, and further, according to the size of the leafs, the protrusion of the protruding rods of the leaf pressing mechanism 10 is adjusted to find a suitable position for pressing the edges of the leaves, and finally the internal defense The fog glass cover 9, the inner atomizing nozzle 8 and the external anti-fog glass cover 13 are installed to form the inner and external spray chamber structures shown in FIG. 1. The external atomizing nozzle 6 and the internal atomizing nozzles 8 are respectively inserted into the external anti-fogging chamber and the observation chamber. The temperature and humidity controller 2 is respectively connected to the external atomizing nozzle 6 and the internal atomizing nozzles 8 through two data lines. The spray nozzle 6 and the spray nozzle 8 are controlled to control the humidity in the spray chamber. The temperature and humidity sensor 7 is placed in the observation room and connected with the data acquisition computer 1 through a data line for detecting the temperature and humidity in the interior anti-fog glass room; the leaf pressing mechanism 10 is set on the support frame 12 in the observation room. The position above the top plate is used to compress the plant leaves 11.

The illumination lamp 5 is located above the external anti-fog cover 13, the first digital camera 3 and the first microscope 4 are placed above the external anti-fog cover 13 and can adjust the first microscope 4 and the external anti-fog cover 13. The relative position between the two is used to obtain the absorption process of the mist droplets on the surface of the leaf surface. The second digital camera 15 and the second microscope 16 are placed on the side of the external anti-fog cover 13 and we can adjust the relative position between the microscope and the external anti-fog cover 13 to obtain the absorption process of the mist on the side of the leaf. The first digital camera 3 and the second digital camera 15 are respectively connected to the data acquisition computer 1 through two data acquisition lines. The data acquisition computer 1 is used for receiving, observing and processing the image of the droplets absorbed by the leaf surfaces transmitted by the first digital camera 3 and the second digital camera 15 and monitoring the humidity in the internal anti-fog glass cover 9.

As shown in FIG. 1, during assembly, the lower base plate 14 is first placed horizontally, and the support frames of the front and side microscopic test systems are placed horizontally on the side of the lower base plate 14. Further, the support frame 12 is horizontally placed above the lower base plate 14, and the plants are placed on the side of the support frame 12 opposite to the support frame 12 of the front and side microscopic test systems. The leaves to be observed are selected and laid out flat on the plate. Above the support frame 12, three protruding rods of the leaf pressing mechanism 10 are immediately adjusted following the size of the leaf, and the leaf are reliably fixed on the upper surface of the support frame 12. In the process, the leaf should be made as much as possible. The pressure piece of the compression mechanism 10 presses against the edge of the leaf to maintain a larger viewing area. Further, the internal anti-fog glass cover 9 is covered and the inner atomizing nozzle 8 is inserted into the nozzle placement hole above the internal anti-fog glass cover 9 to draw out the data signal line of the temperature and humidity sensor 7 and the flow signal control line of the inner atomizing nozzle 8 covering the external anti-fog glass cover 13 and inserting the external atomizing nozzle 6 into the nozzle placement hole above the external anti-fog glass cover 13. The first microscope 4 and the second microscope 16 are assembled on the support rods of the front and side microscopic test systems, and are respectively connected to the first digital camera 3 and the second digital camera 15, finally, the data line is drawn from the digital camera data output port. The output terminals of the data lines of the temperature and humidity sensor 7, the first digital camera 3, and the second digital camera 15 are inserted into the USB interface of the data acquisition computer 1. The flow control signal lines of the internal and external atomizing nozzles are respectively connected to the two interfaces of the temperature and humidity controller 2. The illuminating lamp 5 is fixed on the support rod of the support frame 12 of the frontal and side view microscopic test system through the illuminating lamp holder. At this point, the assembly and connection of the device have been completed. The data acquisition computer 1, the temperature and humidity controller 2, and the illumination lamp 5 are respectively turned on and the spray nozzle starts spraying. First, by adjusting the position of the front and side microscopes to determine a better observation angle, and then adjust the brightness and quality of the image observation by adjusting the axial position of the illumination lamp 5 relative to the supporting rod of the front and side microscopic test system support frame 12, finally started the test of the mist absorption process.

Working process: the leaf to be observed is placed on the upper top plate surface of the support frame 12, and the three protruding rods of the leaf pressure mechanism 10 are adjusted to press the most edge of the leaf to ensure that the leaf has a larger droplet absorption area. The inner anti-fog cover 9 is covered on the upper top plate of the support frame 12, the inner Interior atomization nozzle 8 is inserted into the inner anti-fog cover 9, and then the external anti-fog cover 13 is covered and the front and the second microscope 16 lenses and leafs are Righting, turn on the light 5, connect all data lines and power lines, and then open the data acquisition computer 1 and open the data receiving and processing software or module, and then adjust the lens of the first microscope 4 and the second microscope 16 with respect to the leafs. Distance to determines the most appropriate observation distance, by controlling the temperature and humidity controller 2 to control the internal atomizing nozzle 8 and the external atomizing nozzle 6 to spray and observe the temperature and humidity inside the internal anti-fog glass chamber detected by the temperature and humidity sensor 7, to ensure that The humidity in the anti-fog glass room is equal to 100%. The first digital camera 3 and the second digital camera 15 respectively capture the images enlarged by the first microscope 4 and the second microscope 16.

Specifically, the temperature and humidity controller 2 has two knobs for respectively controlling the atomization amount. The temperature and humidity sensor 7 is DHT11, the temperature measurement range is 0° C.-50° C., and the humidity measurement range is 20%-95%, humidity measurement error is ±5%. The inner atomizing nozzle 8 and the external atomizing nozzle 6 are stepped horn low-frequency ultrasonic atomizing nozzles with an exponential transition section, and the main body has a vibration frequency of 45-60 kHz.

The external anti-fog glass cover 13 has five faces and its dimensions are 620 mm in length, 380 mm in width and 304 mm in height. The material is a common glass coated with conductive material ITO and silicon oxide on the external anti-fog glass cover 13. The surface has a nozzle fixing hole with a diameter of 13 mm. The internal anti-fog glass cover 9 has five faces and its dimensions are: 180 mm in length, 180 mm in width, and 50 mm in height. The material is an ordinary glass coated with conductive material ITO and silicon oxide on the surface thereof, and a fixing hole having a diameter of 13 mm is formed on the upper surface of the internal anti-fog glass cover 9.

The embodiment is a preferred embodiment of the present invention, but the present invention is not limited to the above embodiment, any obvious improvement, substitution or modification that can be made by those skilled in the art without departing from the essence of the present invention belongs to the protection scope of the present invention.

The invention claimed is:

1. A cross-membrane absorption on leaf observation device for a pesticide spray is characterized in that it includes a data acquisition computer, a temperature and humidity controller, a first digital camera, a first microscope, an illumination lamp, an external atomizing nozzle, a temperature and humidity sensor, an internal atomizing nozzle, an internal anti-fog glass cover, a leaf pressing mechanism, a support frame, an external anti-fogging cover, a bottom plate, a second digital camera, and a second microscope;

the external anti-fog glass cover is enveloped on the bottom plate to form an external anti-fog room for placing the whole plant, the support frame is placed in the external atomization chamber, the internal anti-fog glass cover is covered on the upper top plate of the support frame and forms an observation room with the upper top plate of the support frame; the external atomization nozzle and the interior atomization nozzle separately insert the external anti-fog room and the observation room; the temperature and humidity controller is respectively connected to the external atomizing nozzle and the internal atomizing nozzle through two data lines to control the external atomizing nozzle and internal atomizing nozzle to control the humidity in the atomizing chamber;

the temperature and humidity sensor is placed in the observation room and is connected with the data acquisition computer through a data line for detecting the temperature and humidity in the inner anti-fog glass room; the leaf pressing mechanism is set in the observation room located above the upper top plate of the support frame for compacting the plant leaves;

the illumination lamp is located above the external anti-fog cover, the first digital camera and the first microscope are placed above the external anti-fog cover, the relative position between the first microscope and the external anti-fog cover can be adjusted; the position is used to obtain the absorption process of mist droplets on the leaf surface; the second digital camera and the second microscope are placed on the side of the external anti-fog cover to obtain the absorption process of the droplets on the side of the leaf, the relative position between the microscope and the external anti-fog cover can be adjusted; the first digital camera and the second digital camera are respectively connected to the data acquisition computer through two data acquisition lines; the data acquisition computer is used for receiving, observing and processing the image of the mist surface absorption process transmitted by the first digital camera and the second digital camera and monitoring the humidity inside the anti-fog glass cover.

2. The cross-membrane absorption on leaf observation device for a pesticide spray according to claim 1, characterized in that: the leaf pressing mechanism is a manual mechanical leaf edge presser, it comprises a first arc-shaped leaf edge press interior atomization nozzle, a second arc-shaped leaf edge press interior atomization nozzle, an arc-shaped leaf edge press interior atomization nozzle with a single rod without a through-hole, and a single protrusion fixed rod for rods and double-holes, fixed rod for single rods and single-holes, and six connecting rods; the central axis of the cylindrical through-hole of the fixed interior atomization nozzle with the through-hole is parallel to the central axis of the projecting block with the projecting block and the protruding piece of the fixed interior atomization nozzle in the same horizontal plane; the nominal diameter of the through-hole and the protruding rod are both 10 mm; the clearance between any of the through-holes and the protruding rod adopts a clearance fit; the protruding rod of the arc-shaped leaf edge pressing interior atomization nozzle without a through-hole is inserted firstly; the single through rod and the through-hole of the single through-hole fixing interior atomization nozzle, and then the two through-holes of the single protruding rod and the fixing interior atomization nozzle of the double through-hole are respectively put on the already connected single extension; extruded rod-shaped arc-shaped leaf edge pressure interior atomization nozzle and single rod and single hole through the fixed interior atomization nozzle on the protruding rod; finally, all the pressure pieces and the fixing pieces are connected to form 10 living hinges with the six connecting rods; the single projecting rod and the single through-hole fixing interior atomization nozzle are fixedly connected to the support frame by welding; the first arcuate leaf edge pressure piece and the second arcuate leaf edge pressure, the height of the interior atomization nozzle is 15 mm, the length of the projecting rod of the arc-shaped leaf edge compact without the through-hole of the single projecting rod is 60 mm, and the single projecting rod and the single through-hole are fixed; the projecting rod length of the interior atomization nozzle is 45 mm, the projecting rod length of the single projecting rod and the fixed interior atomization nozzle of the double through-hole is 30 mm, and the thicknesses of the six connecting rods are both 3 mm.

3. The cross-membrane absorption on leaf observation device for a pesticide spray according to claim 1, characterized in that: the temperature and humidity controller has two knobs for controlling the atomization amount, respectively; the atomizing nozzle and the external atomizing nozzle are stepped horn low-frequency ultrasonic atomizing nozzles with an exponential transition section, the main body of which has a vibration frequency of 45-60 kHz.

4. The cross-membrane absorption on leaf observation device for a pesticide spray according to claim 1, characterized in that: the first digital camera and the second digital camera respectively capture images enlarged by the first microscope and the second microscope.

5. The cross-membrane absorption on leaf observation device for a pesticide spray according to claim 1, characterized in that: the temperature and humidity sensor model is DHT11, the temperature measurement range is 0° C.-50° C., the humidity measurement range is 20%-95%, and the humidity measurement error is ±5%.

6. The cross-membrane absorption on leaf observation device for a pesticide spray according to claim 1, characterized in that: the external anti-fog glass cover has five surfaces and its dimensions are: 620 mm in length, 380 mm in width, 304 mm in height; the material is a glass coated with conductive material ITO and silicon oxide on the surface thereof, and a nozzle fixing hole having a diameter of 13 mm is opened on the external surface of the external anti-fog glass cover.

7. The cross-membrane absorption on leaf observation device for a pesticide spray according to claim 1, characterized in that: the internal anti-fog glass cover has five faces and its dimensions are: 180 mm in length, 180 mm in width, 50 mm in height; the material is a common glass coated with conductive material ITO and silicon oxide on the surface, and a fixing hole having a diameter of 13 mm is opened on the upper surface of the internal anti-fog glass cover.

* * * * *